(12) United States Patent
Stankus et al.

(10) Patent No.: US 9,180,228 B2
(45) Date of Patent: Nov. 10, 2015

(54) RUBBER TOUGHENED BIORESORBABLE POLYMER PERIPHERAL SCAFFOLDS

(75) Inventors: John Stankus, Campbell, CA (US); Yunbing Wang, Sunnyvale, CA (US); Mikael Trollsas, San Jose, CA (US); Syed Faiyaz Ahmed Hossainy, Hayward, CA (US); Michael H. Ngo, San Jose, CA (US); Dariush Davalian, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 13/252,120

(22) Filed: Oct. 3, 2011

(65) Prior Publication Data
US 2013/0085563 A1    Apr. 4, 2013

(51) Int. Cl.
| | |
|---|---|
| *A61F 2/06* | (2013.01) |
| *A61L 31/12* | (2006.01) |
| *A61L 31/04* | (2006.01) |
| *A61L 31/14* | (2006.01) |
| *A61F 2/915* | (2013.01) |

(52) U.S. Cl.
CPC ............... *A61L 31/129* (2013.01); *A61F 2/915* (2013.01); *A61L 31/041* (2013.01); *A61L 31/141* (2013.01); *A61L 31/148* (2013.01); *A61F 2230/0013* (2013.01); *A61F 2230/0054* (2013.01)

(58) Field of Classification Search
CPC .................................................. A61F 2/915
USPC ........................................................ 623/1.15
See application file for complete search history.

(56) References Cited

U.S. PATENT DOCUMENTS

| | | | |
|---|---|---|---|
| 7,964,210 B2 | 6/2011 | Wang et al. | |
| 2003/0208259 A1* | 11/2003 | Penhasi | 623/1.15 |
| 2005/0010275 A1* | 1/2005 | Sahatjian et al. | 623/1.11 |
| 2005/0245637 A1* | 11/2005 | Hossainy et al. | 523/113 |
| 2005/0245719 A1* | 11/2005 | Mather et al. | 528/60 |
| 2006/0020324 A1* | 1/2006 | Schmid et al. | 623/1.16 |
| 2007/0050018 A1* | 3/2007 | Wainwright | 623/1.51 |
| 2007/0182041 A1 | 8/2007 | Rizk et al. | |
| 2007/0224234 A1 | 9/2007 | Steckel et al. | |
| 2007/0231365 A1 | 10/2007 | Wang et al. | |
| 2007/0283552 A1 | 12/2007 | Gale et al. | |
| 2008/0015686 A1 | 1/2008 | Gale et al. | |
| 2008/0147165 A1 | 6/2008 | Hossainy et al. | |
| 2008/0243228 A1 | 10/2008 | Wang et al. | |
| 2008/0275537 A1 | 11/2008 | Limon | |
| 2009/0012604 A1 | 1/2009 | Schmitz et al. | |
| 2009/0088835 A1 | 4/2009 | Wang | |
| 2009/0143853 A1* | 6/2009 | Morris et al. | 623/1.16 |

(Continued)

FOREIGN PATENT DOCUMENTS

WO    WO2007/092417    8/2007

OTHER PUBLICATIONS

International Search Report for PCT/US2012/043357 mailed Sep. 5, 2012, 7 pgs.

(Continued)

*Primary Examiner* — Jacqueline Woznicki
(74) *Attorney, Agent, or Firm* — Squire Patton Boggs (US) LLP

(57) ABSTRACT

Bioabsorbable scaffolds are disclosed with a rigid polymer component and a rubbery polymer component. The rubbery polymer component is miscible, partially miscible, or immiscible with the rigid polymer component.

9 Claims, 5 Drawing Sheets

(56) References Cited

U.S. PATENT DOCUMENTS

2009/0182415 A1    7/2009  Wang
2010/0004735 A1*   1/2010  Yang et al. ............... 623/1.16
2010/0026223 A1    2/2010  Liu et al.
2010/0262223 A1*  10/2010  Kleiner .................... 623/1.15
2011/0066222 A1*   3/2011  Wang et al. ............... 623/1.15
2011/0190871 A1*   8/2011  Trollsas et al. ........... 623/1.15
2011/0190872 A1*   8/2011  Anukhin et al. ........... 623/1.16

OTHER PUBLICATIONS

Van Vlack, Elements of Materials Science and Engineering 6$^{th}$ Ed., Addison-Wesley Publishing Co, pp. 270-271 (1989).

Wang et al., "Polyethylene-Poly(L-lactide) Diblock Copolymers: Synthesis and Compatibilization of Poly(L-lactide)/Polyethylene Blends", J. of Polymer Science vol. 39, issue 16, pp. 2755-2766 (2001).

* cited by examiner

RUBBER TOUGHENED BIORESORBABLE POLYMER PERIPHERAL SCAFFOLDS

BACKGROUND OF THE INVENTION

1. Field of the Invention

This invention relates polymeric medical devices, in particular, bioresorbable stents or stent scaffoldings.

2. Description of the State of the Art

This invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. A medicated stent may be fabricated by coating the surface of either a metallic or polymeric scaffold with a polymeric carrier that includes an active or bioactive agent or drug. Polymeric scaffolds may also serve as a carrier of an active agent or drug. An active agent or drug may also be included on a scaffold without being incorporated into a polymeric carrier.

The stent must be able to satisfy a number of mechanical requirements. The stent must be capable of withstanding the structural loads, namely radial compressive forces, imposed on the scaffold as it supports the walls of a vessel. Therefore, a stent must possess adequate radial strength. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation. Radial strength is measured either by applying a compressive load to a stent between flat plates or by applying an inwardly-directed radial load to the stent.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Some treatments with stents require its presence for only a limited period of time. Once treatment is complete, which may include structural tissue support and/or drug delivery, it may be desirable for the stent to be removed or disappear from the treatment location. One way of having a stent disappear may be by fabricating a stent in whole or in part from materials that erodes or disintegrate through exposure to conditions within the body. Stents fabricated from biodegradable, bioabsorbable, bioresorbable, and/or bioerodable materials such as bioabsorbable polymers can be designed to completely erode only after the clinical need for them has ended.

The development of a bioresorbable stent or scaffold could obviate the permanent metal implant in vessel, allow late expansive luminal and vessel remodeling, and leave only healed native vessel tissue after the full absorption of the scaffold. A fully bioresorbable stent can reduce or eliminate the risk of potential long-term complications and of late thrombosis, facilitate non-invasive diagnostic MRI/CT imaging, allow restoration of normal vasomotion, and provide the potential for plaque regression.

To treat peripheral vascular disease percutaneously in the lower limbs is a challenge with current technologies. Long term results are sub-optimal due to chronic injury caused by the constant motions of the vessel and the implant as part of every day life situations. To reduce the chronic injury a bioresorbable scaffold for the superficial femoral artery (SFA) and/or the popliteal artery can be used so that the scaffold disappears before it causes any significant long term damage. One of the challenges with the development of a longer length scaffold (5-25 cm) is the high risk for fatigue influenced strut fractures prior to the intended bioresorption time especially when implanted in the superficial femoral artery.

A scaffold in the SFA and/or the popliteal artery is subjected to various non-pulsatile forces, such as radial compression, torsion, flexion, and axial extension and compression. These forces place a high demand on the scaffold mechanical performance and can make the scaffold more susceptible to fracture than less demanding anatomies. In addition to high radial strength, stents or scaffolds for peripheral vessels such as the SFA, require a high degree of crush recovery. The term "crush recovery" is used to describe how the scaffold recovers from a pinch or crush load, while the term "crush resistance" is used to describe the force required to cause a permanent deformation of a scaffold.

Therefore, an important goal for treatment of the SFA and/or the popliteal artery is the development of bioabsorbable scaffold with high radial strength, high crush recovery, and high resistance to fracture or high toughness.

Incorporation by Reference

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

SUMMARY OF THE INVENTION

Various embodiments of the present invention include a stent comprising a scaffold formed from a polymer tube, configured for being crimped to a balloon, the scaffold having a pattern of interconnected elements and the scaffold having an expanded diameter when expanded from a crimped state by the balloon, wherein the scaffold attains greater than about 80% of its diameter after being crushed to at least 50% of its expanded diameter; and wherein the scaffold has a radial stiffness greater than 0.3 N/mm and wherein the scaffold is made from a composition including a rigid bioresorbable polymer component having a glass transition temperature (Tg) greater than 37 deg C. and a rubbery polymer component having a Tg less than ambient temperature, wherein the rubbery polymer component is between 5 and 25 wt % of the composition.

Further embodiments of the present invention include a stent comprising a scaffold made from a bioresorbable composition comprising a bioresorbable rigid polymer component having a Tg greater than 37 deg C. and a rubbery polymer component having a Tg less than ambient temperature, wherein the rubbery polymer component is partially or completely miscible in the rigid polymer component, wherein the Mw of the rubbery polymer component is 20 kDa or less.

Additional embodiments of the present invention include a stent comprising a scaffold made from a bioresorbable composition comprising a bioresorbable random copolymer including a bioresorbable rigid polymer having a Tg greater than 37 deg C. and a rubbery polymer having a Tg less than ambient temperature, wherein the rubbery polymer is 5 to 25 mol % of the scaffold.

Other embodiments of the present invention include a stent comprising a scaffold made from a bioresorbable composition comprising a bioresorbable rigid polymer component having a Tg greater than 37 deg C. and a rubbery polymer component having a Tg less than ambient temperature, wherein the Mw of the rubbery polymer component is less than 50% of the Mw of the bioresorbable rigid polymer component, wherein the bioresorbable rigid polymer component is 75 to 95 wt % of the scaffold and the rubbery polymer component is 5 to 25 wt % of the scaffold.

Further embodiments of the present invention include a method of fabricating a stent comprising: providing a tube made of a bioresorbable polymer composition including a matrix phase and dispersed phase composed of domains distributed throughout the matrix phase, wherein the matrix phase comprises a bioresorbable rigid polymer with a Tg greater than 37 deg C. and the dispersed phase comprises a rubbery polymer with a Tg less than ambient temperature; elongating the tube along its cylindrical axis at least 50%, wherein the elongation elongates the domains in the direction of the cylindrical axis; and fabricating a scaffold from the tube after the elongating step, wherein the composition of the scaffold includes elongated domains.

Additional embodiments of the present invention include a stent comprising a scaffold made from a bioresorbable polymer composition including a matrix phase and a dispersed phase composed of domains distributed throughout the matrix phase, wherein the matrix phase comprises a bioresorbable rigid polymer with a Tg greater than 37 deg C. and the dispersed phase comprises a crosslinked rubbery polymer which is crosslinked with the rigid polymer.

Further embodiments of the present invention include a method of fabricating a stent comprising: providing a tube or a scaffold made of a bioresorbable polymer composition including a matrix phase and a dispersed phase composed of domains distributed throughout the matrix phase, wherein the matrix phase comprises a bioresorbable rigid polymer with a Tg greater than 37 deg C. and the dispersed phase comprises a rubbery polymer with a Tg less than ambient temperature; irradiating the tube or the scaffold to induce crosslinking of the rubbery polymer and the rubbery polymer to the rigid polymer; and if the tube is irradiated, fabricating a scaffold from the tube after the irradiating step.

DETAILED DESCRIPTION OF THE INVENTION

The methods described herein are generally applicable to any amorphous or semi-crystalline polymeric implantable medical device, especially those that have load bearing portions when in use or have portions that undergo deformation during use. In particular, the methods can be applied to tubular implantable medical devices such as self-expandable stents, balloon-expandable stents, and stent-grafts.

Figure 1:
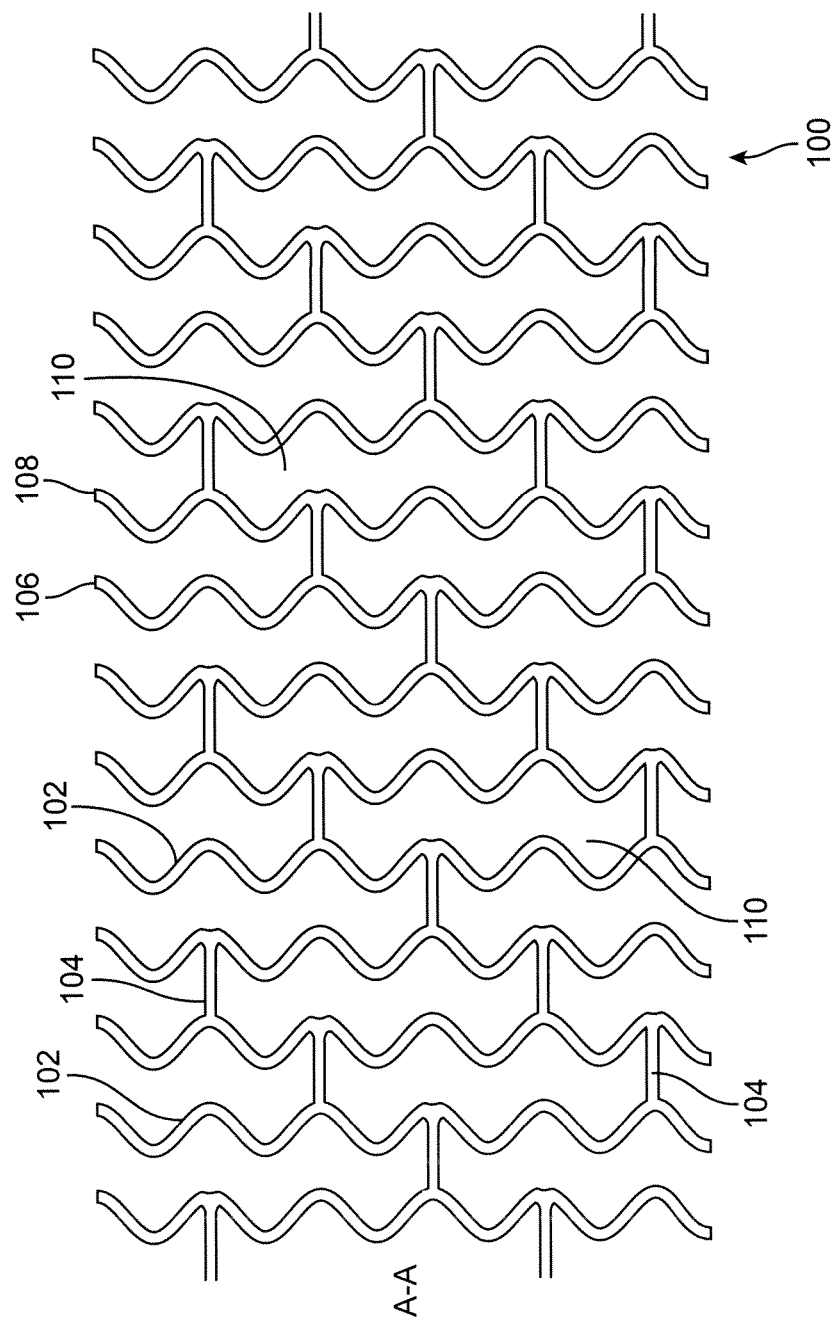
FIG. 1 depicts a stent.

FIG. 1 illustrates a portion of an exemplary stent or scaffold pattern 100. The pattern 100 of FIG. 1 represents a tubular scaffold structure so that an axis A-A is parallel to the central or longitudinal axis of the scaffold. FIG. 1 shows the scaffold in a state prior to crimping or after deployment. Pattern 100 is composed of a plurality of ring struts 102 and link struts 104. The ring struts 102 forms a plurality of cylindrical rings, for example, rings 106 and 108, arranged about the cylindrical axis A-A. The rings are connected by the link struts 104. The scaffold comprises an open framework of struts and links that define a generally tubular body with gaps 110 in the body defined by rings and struts. The cylindrical tube of FIG. 1 may be formed into this open framework of struts and links described by a laser cutting device that cuts such a pattern into a thin-walled tube that may initially have no gaps in the tube wall.

A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

A stent or scaffold of the present invention can be made partially or completely from a biodegradable, bioresorbable, and bioabsorbable polymer. The stent can also be made in part of a biostable polymer. A polymer for use in fabricating stent can be biostable, bioresorbable, bioabsorbable, biodegradable or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

An exemplary embodiment used in the studies described herein has the stent pattern described in U.S. application Ser. No. 12/447,758 (US 2010/0004735) to Yang & Jow, et al. Other examples of stent patterns suitable for PLLA are found in US 2008/0275537. An exemplary cross-section of the struts of a scaffold is 150×150 microns. Such scaffolds may further include a polymer coating which optionally includes a drug. The coating may be conformal (around the perimeter of the scaffold) and may be 2-5 microns thick. In other embodiments described herein, the scaffolds may be made partly out of the composite.

Exemplary stent scaffold patterns for the SFA are disclosed in US2011/0190872 and US2011/0190871. As compared to coronary stents, a peripheral (SFA) stent scaffold usually has lengths of between about 36 and 40 mm or even between 40 and 200 mm when implanted in the superficial femoral artery, as an example. The scaffold for SFA may have a pre-crimping diameter of between 5-10 mm, or more narrowly 6-8 mm, and can possess a desired pinching stiffness while retaining at least a 80% recoverability from a 50% crush. The scaffold for SFA may have a wall thickness of about 0.008" to 0.014" and configured for being deployed by a non-compliant balloon, e.g., 6.5 mm diameter, from about a 1.8 to 2.2 mm diameter (e.g., 2 mm) crimped profile. The SFA scaffold may be deployed to a diameter of between about 4 mm and 7 mm.

Bioressorbable stents can be useful for treatment of various types of bodily lumens including the coronary artery, superficial femoral artery, popliteal artery, neural vessels, and the sinuses. In general, these treatments require the stent to provide mechanical support to the vessel for a period of time and then desirably to absorb away and disappear from the implant site. The important properties of a bioabsorbable stent or scaffolding include mechanical and degradation properties. The mechanical requirements include high radial strength, high radial stiffness, and high fracture toughness. The degradation properties include the absorption profile, for example, the change in molecular weight, radial strength, and mass with time. Specific aspects of the absorption profile include the time that the stent maintains radial strength before starting to decrease and the total absorption time or absorption time (complete mass loss from implant site).

A stent scaffolding made from a bioresorbable polymer may be designed to maintain its radial strength and/or radial stiffness once implanted to provide mechanical support to the vessel for a prescribed time period and maintain patency of the lumen. The radial strength must be sufficiently high initially to support the lumen at a desired diameter. The period of time that the scaffold is required or desired to maintain patency depends on the type of treatment, for coronary treatment it is about 3 months. After this time period, the vessel is healed sufficiently to maintain an expanded diameter without support. Therefore, after this time period, the scaffolding may start to lose radial strength and/or radial stiffness due to molecular weight degradation. As the scaffolding degrades further, it starts to lose mechanical integrity and then experiences mass loss and eventually absorbs away completely or there are negligible traces left behind.

Ideally, it is desired that once the stent support is no longer needed by the lumen, the bioressorbable scaffold should be ressorbed as fast as possible while also meeting all basic safety requirements during its degradation period. Such safety requirements can include a gradual disintegration and resorpton that does not allow release of fragments that could cause adverse events such as thrombosis. In this way, the stent scaffold enables the vessel healing as well as enabling the advantages mentioned herein of a bioressorbable scaffold to the greatest extent. It is desirable for a bioresorbable scaffold to have an absorption time of about 18 to 26 months for coronary vascular application, of about eighteen months (e.g., 16-20 months) for a peripheral application (e.g., superficial femoral artery (SFA)) and/or politeal artery), 18-24 months for neural applications, and less than a year for nasal applications.

With respect to radial strength and stiffness, a stent should have sufficient radial strength and/or stiffness to withstand structural loads, namely radial compressive forces, imposed on the stent so that the stent can supports the walls of a vessel at a selected diameter for a desired time period. A polymeric stent with adequate radial strength and/or stiffness enables the stent to maintain a lumen at a desired diameter for a sufficient period of time after implantation into a vessel.

In addition, the stent should possess sufficient toughness or resistance to fracture to allow for crimping, expansion, and cyclic loading without fracture or cracking that would compromise the function of the stent. The toughness or resistance to fracture can be characterized for a material by the elongation at break and for a stent by the number and degree of cracks in a scaffold during use, such as after crimping or deployment. These aspects of the use of the stent involve deformation of various hinge portions of the structural elements of the scaffold.

Some bioresorbable polymers, for example, semi-crystalline polymers, are stiff or rigid under physiological conditions within a human body and have been shown to be promising for use as a scaffold material. Specifically, polymers that have a glass transition temperature (Tg) sufficiently above human body temperature which is approximately 37° C., should be stiff or rigid upon implantation. Poly(L-lactide) (PLLA) is attractive as a stent material due to its relatively high strength and a rigidity at human body temperature, about 37° C. As shown in Table 1, PLLA has high strength and tensile modulus compared to other biodegradable polymers. Since it has a glass transition temperature well above human body temperature, it remains stiff and rigid at human body temperature. This property facilitates the ability of a PLLA stent scaffolding to maintain a lumen at or near a deployed diameter without significant recoil (e.g., less than 10%).

Other rigid bioresorbable polymers include poly(D-lactide) (PDLA), polyglycolide (PGA), and poly(L-lactide-co-glycolide) (PLGA). The PLGA include those having a mole % of (LA:GA) of 85:15 (or a range of 82:18 to 88:12), 95:5 (or a range of 93:7 to 97:3), or commercially available PLGA products identified being 85:15 or 95:5 PLGA. Rigid polymers may refer to polymers that have a Tg higher than human body temperature or within 5 deg C. of human body temperature.

TABLE 1

Comparison of properties of bioressorbable polymers.

|  | Tm (° C.) | Tg (° C.) | Tensile Strength (MPa) | Tensile Modulus (MPa) | Elongation at break (%) | Absorption Rate |
|---|---|---|---|---|---|---|
| PLLA | 175 | 65 | 28-50 | 1200-2700 | 6 | 1.5-5 years |
| P4HB | 60 | −51 | 50 | 70 | 1000 | 8-52 weeks |
| PCL | 57 | −62 | 16 | 400 | 80 | 2 years |
| PDO | 110[1] | −10[1] | 1.5[1,2] | 30[2] | 35[3] | 6-12[1] 6[2] |
| PGA | 225 | 35 | 70 | 6900 | <3 | 6 weeks |
| DL-PLA | Amorphous | 50-53 | 16 | 400 | 80 | 2 years |
| P3HB | 180 | 1 | 36 | 2500 | 3 | 2 years |

PLLA (poly(L-lactide);
P4HB (poly-4-hyroxybutyrate);
PCL (polycaprolactone);
PGA (polyglycolide);
DL-PLA (poly(DL-lactide);
P3HB (poly-3-hydroxybutyrate);
PDO (p-polydioxanone)
All except PDO, Martin et al., Biochemical Engineering 16 (2003) 97-105.
[1]Medical Plastics and Biomaterials Magazine, March 1998.
[2]Medical Device Manufacturing & Technology 2005.
[3]The Biomedical Engineering Handbook, Joseph D. Bronzino, Ed. CRC Press in Cooperation with IEEE Press, Boca Raton, FL, 1995.

The strength stiffness, and the fracture toughness of such polymers can be improved through various processing methods (e.g., radial expansion and suitable choice of associated processing parameters). However, there is still strong incentive to improve upon polymers such as PLLA as scaffold materials not only for coronary applications, but to tailor it for other peripheral applications as well. It is important not only to improve the strength of such polymers, but also to improve the fracture toughness to reduce or avoid cracked or broken struts prior to the designed bioresorption time period.

A bioresorbable scaffold with enhanced fracture resistance may be composed of blends of a load bearing rigid or stiff polymer with that of a high toughness polymer, for example, a rubbery polymer. The load bearing stiff polymer is called the matrix, since the majority of the rubber toughened material is composed of the stiff polymer. A rubbery polymer may have a modulus that is less than the rigid polymer and/or an elongation at break greater than then rigid polymer. In some instances, the rubbery polymer can be immiscible, partially miscible or miscible with the rigid polymer.

An immiscible or partially miscible rubbery polymer can form a dispersed, rubbery phase within a matrix phase which includes plurality of discrete regions or domains that are dispersed within and throughout the stiff polymer. The matrix, matrix phase, or continuous phase contains all or primarily rigid polymer.

It is believed that the dispersed rubbery bioresorbable polymer domains may induce energy dissipation in the more stiff material and retard crack initiation and propagation to improve fracture toughness of the blend. Bonding or interfacial adhesion between the phases can facilitate enhancement of fracture toughness. It is believed that bonding between the phases helps a highly dispersed phase remain stable and provides uniform energy transfer forfracture interruption, and thus improved fracture resistance. See, Y. Wang, etc. Journal of Polymer Science Part A: Polymer Chemistry, 39, 2001, 2755-2766. Insufficient adhesion between phases can result in a dispersed phase that is unstable and thus phase separates further from the matrix resulting in agglomeration and high plastic deformation. Energy transfer may be enhanced if the rubbery polymer is at least partially miscible with the stiff polymer.

A partially miscible or miscible rubbery polymer can also increase fracture toughness of a stiff polymer through plasticizing of the stiff polymer. Plasticizing refers generally to increasing the plasticity of a material. Plasticity or plastic deformation describes the deformation of a polymer undergoing non-reversible changes of shape in response to applied forces. A rubbery polymer that plasticizes a stiff polymer increases its flexibility and toughness, thereby, increasing resistance to fracture. Without being limited by theory, a rubbery polymer plasticizer works by embedding between the chains of a stiff polymer, spacing them apart (increasing the "free volume"), and thus significantly lowering the glass transition temperature for the stiff polymer and making it softer.

A more fracture tough bioresorbable scaffold may be made by melt blending of a rubbery bioresorbable polymer with a stiffer polymer such as poly(L-lactide) (PLLA). The ability to rubber toughen the scaffold while still maintaining an adequate level of mechanical strength and stiffness will enable the scaffold to be implanted and treat many disease states where mechanical fatigue and fracture would be a concern with a scaffold that includes only stiff polymer-based scaffolds. Rubber toughening of scaffolds has been disclosed previously, for example, in 2008/0147165.

Embodiments of the present invention include stent scaffolds, in particular peripheral artery scaffolds, composed of a rubber toughened material. The rubber toughened (RT) material includes a rigid or matrix polymer component and a rubbery polymer component. The rubbery polymer component can refer to a rubbery polymer (e.g., PCL, P4HB, etc.), a rubbery polymer block of a block copolymer, or the rubbery polymer component of a random or alternating copolymer.

The stent scaffolds may be formed by extruding polymer tubes made of the rubber toughened material and laser cutting the tubes to form a scaffold. The rubbery component increases the fracture resistance of the stent scaffold by forming discrete rubbery domains, plasticizing, or both. In some embodiments, the rubbery polymer is completely miscible in the stiff polymer and the increase in toughness is due to plasticizing.

Examples of biodegradable rubbery polymers include but are not limited to polyhydroxyalkanoates (PHA), poly(4-hydroxybutyrate) (P4HB), poly(ε-caprolactone), (PCL) poly(trimethylene carbonate) (PTMC), poly(butylene succinate) (PBS), poly(p-dioxanone) (PDO), and poly(ester amides) (PEA). Copolymers of the above rubber polymers with a rigid polymer such as PLLA can also be blended with the matrix polymer. These can include block copolymers, random copolymers, alternating polymers, and segmented polymers.

The above rubbery polymers are hydrophobic. Hydrophilic polymers can also provide increased fracture toughness through phase separation and/or plasticizing when blended with a matrix polymer and will also be referred to as rubbery polymers. The hydrophilic polymers can be bioresorbable, water soluble, gel forming, or any combination thereof. Such polymers include polyethylene oxide (PEO) or polyethylene glycol (PEG), and polyvinylpyrrolidone (PVP), polyvinyl alcohol (PVA). Rubbery polymers may also include amphiphilic block copolymers such as PEG-PPO (polypropylene oxide), and PEG-PLLA. Unlike hydrophobic polymers, hydrophilic polymers such as PEG and PVA tend to swell due to uptake of water upon exposure to moisture. Thus, the rubber toughening effects due to such polymers tends to be dramatically different in wet and dry conditions. Thus, the fracture toughness of a scaffold containing a hydrophilic rubbery polymer such as PEG increases when exposed to bodily fluids upon implantation.

Either one of the hydrophilic or the hydrophobic polymers may also improve fracture resistance and toughness by plasticizing the matrix. As indicated above, plasticizing arises through partial or complete miscibility of the rubbery polymer in the stiff polymer. Miscibility of a rubbery polymer in a stiff polymer depends generally on the molecular weight and concentration of the rubbery polymer in the stiff polymer. Miscibility or partial miscibility of a selected rubbery polymer-stiff polymer pair may be achieved when the molecular weight and/or concentration of the rubbery polymer is sufficiently low. Thus, rubbery polymer plasticizers are usually lower in molecular weight and also at lower concentrations in the matrix.

Exemplary potential rubbery polymer plasticizers include polyethylene oxide (PEO) or polyethylene glycol (PEG), polyvinylpyrrolidone (PVP), polyvinyl alcohol (PVA), PCL, P4HB and other well known plasticizers mentioned in the literature. Such rubbery polymer plasticizers may plasticize stiff polymers such as PLLA and PLGA. For complete miscibility, the molecular weight of the rubbery polymer plasticizers may be less than 2000 Da, 600 to 1000 Da, 1000 to 1500 Da, 1500 to 2000 Da. The concentration of the rubbery plasticizer in the stiff polymer may be 1 to 5 wt %, 4 to 6 wt %, 5 to 10 wt %, or 5 to 25 wt % of the scaffold. As described in more detail below, at higher molecular weights that are below the rigid polymer molecular weight, the rubbery polymer may have partial miscibility in the stiff polymer, and thus still provide plasticization even with phase separation into rubbery domains.

Additionally, the rubbery polymers can have various structures. The structures include linear structures and branched structures. Branched structures include star polymers, hyperbranched polymers, and dendritic polymers. For example, the rubbery polymer can be a branched polycaprolactone, such as a star polycaprolactone (3, 4, or more arms), or hyperbranched polycaprolactone. The branched polymers can also be block copolymers such as star poly(caprolactone-co-lactide) (3, 4, or more arms) or alternatively star poly(lactide-co-caprolactone) (3, 4, or more arms). The branching provides stability to a polymer blend by reducing or preventing polymer reptation movements.

Some embodiments of the rubber toughened scaffolds include blends of rigid polymers and rubbery polymers. In these embodiments, the blend may be composed of a rigid polymer such as PLLA and a rubbery polymer. Examples include a blend of PLLA with PCL, P4HB, and PEG. In such embodiments, immiscible or partially miscible rubbery polymers form a dispersed phase with domains distributed throughout a matrix phase composed of the rigid polymer.

Additionally, block copolymers that include rubbery segments may be blended with a matrix polymer to increase fracture toughness. These block copolymers include blocks or segments of polymers for example, polymer segment A bonded to polymer segment B, that are covalently bonded in various configurations. Polymer segment A may be a matrix polymer segment and polymer segment B may be a rubbery polymer segment.

The different polymer segments of a block copolymer can be immiscible or partially miscible and can phase separate into microphase domains despite being directly or indirectly covalently bonded. Such domains include matrix phase domains that include the rigid polymer segments and rubbery phase domains that include rubbery segments. Blends of such block copolymers with rigid polymers are disclosed in U.S. Pat. No. 7,964,210 and. US2009/0088835. Block copolymers can also include polyurethane segmented block copolymers in which polymer segments are joined by a urethane linkage, as disclosed in US2009/0182415.

In the blends of the block copolymers and matrix polymers, the matrix polymer may be the same as the rigid polymer segments, as in a blend of PLLA and PLLA-b-PCL. Therefore, the rigid polymer blocks, e.g., PLLA block, may phase separate into the matrix polymer phase and the rubbery polymer segments will form microphase domains.

These block copolymers can include linear block copolymers such as diblock (AB), triblock (ABA), or, generally, multiblock copolymers (ABABA). ABA triblock polymers can have A as a rigid block (e.g., PLLA) and B as a rubbery block (e.g., PCL or PTMC).

Exemplary rubbery block copolymers include PLLA-b-PCL, PLLA-b-PCL-b-PLLA; and PLLA-b-PEG. Other exemplary linear block copolymers are disclosed in US2009/0088835.

The block copolymers can also include star-block and branched copolymers. Star block copolymers can include at least three arms, the arms corresponding to polymer chains. The blocks at the core of the star blocks may include rubbery polymer blocks and outer blocks that are rigid polymer blocks (e.g., PLLA). It is believed that the outer blocks may act as anchors to provide physical crosslinking points serving to bind the rigid polymer matrix to the rubbery phase which may help maintain the rubbery phase in a deformed state. Alternatively, the blocks at the core can be rigid polymer segments and the outer segments are rubbery polymer segments. Exemplary star block copolymers are disclosed in US2008/0243228 and US2009/0088835.

Additional block copolymers with rubbery and rigid blocks include hyperbranched-like polymers, comb-like polymers, dendrimer-like star polymers, and dendrimers.

Additionally, random or alternating copolymers of rubbery polymers and rigid polymers may be blended with a matrix polymer to increase fracture toughness. Exemplary copolymers include PLLA-co-PCL, PLLA-co-PDO, or PLLA-co-PTMC. The rigid polymer of the copolymer may be the same as the matrix polymer, for example, PLLA blended with PLLA-co-PCL. The copolymer may be miscible with the matrix polymer, partially miscible with the matrix polymer, or immiscible with the matrix polymer.

In further embodiments, a scaffold may be composed of a ternary blend that includes a rigid polymer, a rubbery polymer, and a block copolymer with rigid and rubbery blocks, as described herein. The block copolymer is included to stabilize the domain structure of the rubbery polymer phase dispersed in the matrix polymer phase. The block copolymer has segments of the rubbery polymer and rigid polymer and acts as a compatibilizer between the rubbery domains and matrix phase. The block copolymer provides better interfacial bonding through partially miscible chain and chain entanglement. Random copolymers with high molar ratio of rubbery polymer to stiff polymer (e.g., >20:80) can also provide the stabilization.

Additionally, a scaffold can be composed completely or almost completely of a block copolymer including a rigid and rubber blocks. Additionally, a scaffold can be composed completely or almost completely of a random copolymer including a rigid and rubber blocks. The rigid polymer components of these copolymers provide strength and stiffness for structural support and the rubber polymer component increases the fracture toughness of the scaffold.

The rubber toughening or increase in the fracture resistance of a stiff and brittle polymer, such as a biodegradable polyester, depends on several variable or conditions, some of which are interrelated. These include the Tg and Tm of the rubbery polymer; size, shape and distribution of a rubbery phase; amount of rubbery component (wt % or mol % of scaffold composition); molecular weight of rubbery component, relative molecular weight of rubbery component and rigid component; and thermodynamic miscibility X value of the polymer with matrix polymer.

The rubbery component has a Tg, less than the matrix polymer, e.g., at least 10, 20, 30, 40, or at least 50 deg C. less). The Tg of the rubbery component may have a Tg lower than ambient temperature or the physiological temperature (37° C.) of the patient. Ambient temperature is between 20 to 30 deg C. or any value or sub-range within this range.

As indicated, a rubbery component that is immiscible or partially miscible in a rigid polymer component may distribute in small domains dispersed within a rigid polymer or matrix phase. The uniformity of the dispersion of the rubber domains in the stiff polymer component is important to increasing the fracture resistance. To achieve a uniform dispersion, the rubbery polymers may be blended in solution or in the melt. Examples of melt processing methods may include but are not limited to physical blending of pellets, extrusion, injection molding, compounding extrusion with co-rotating or counter-rotating twin screws, electrospinning, etc.

Additionally, it is expected that decreasing the size of the rubbery domains may increase the fracture resistance of the scaffold composition. The characteristic length (diameter, length, width) of a discrete phase can be 250 nm-5 um, or more narrowly 250 nm to 100 nm, 100 nm to 500 nm, 500 nm to 1 μm, 1 μm to 2 μm, 2 μm to 5 μm, or greater than 5 μm.

The distribution and size of the rubber domains depends on several factors including the processing conditions in forming scaffold composition, miscibility of the polymer components, and adhesion of the rubbery domains with the matrix phase. As discussed herein, the miscibility and adhesion depend in part on the molecular weight of the rubbery polymer component and the relative molecular weight of the rubber and stiff polymer component. Additionally, rubber toughening depends on the shape of the rubbery domains, since, increasing anisotropy of the domain shape increases the surface to volume interaction of the rubbery phase with the matrix phase which enhances rubber toughening.

In order to decrease the blend stiffness, a scaffold composition may have at least 0.2 to 1 wt %, 1-5 wt %, 5 to 15 wt %, and 15-25% of a rubbery polymer component. The remainder of the composition maybe a stiff polymer component or could include other additives or components (e.g., less than 1 to 5 wt %) in addition to the rigid polymer component. The rubbery polymer component may be a rubbery polymer blended with a matrix polymer, rubbery polymer blocks of a block copolymer, or rubber polymer of a random or alternating copolymer.

An effective amount of rubbery component is at least enough to provide a desired increase in fracture resistance and below an amount that results an undesired reduction in stiffness or modulus of the scaffold composition, so that the scaffold can maintain an expanded diameter. As discussed herein, the effective amount depends in part on the miscibility of the rubbery polymer component with the rigid polymer component. The effective amount depends also on interfacial adhesion, which depends in part on the molecular weight of the rubbery polymer component and the relative molecular weight of the rubber and stiff polymer components.

For rubbery components that form dispersed domains, the rubbery polymer component molecular weight is high enough to form such domains and to provide the rubbery mechanical properties of the rubbery polymer. A general threshold number average molecular weight may between 20 and 100 kDa to exhibit sufficient mechanical properties.

In general, the miscibility of a polymer in another polymer varies with molecular weight of the polymer. It is expected that partial miscibility is increased as the rubbery polymer MW decreases. As indicated above, it is believed that partially miscibility of a rubbery polymer component in a matrix phase can enhance rubber toughening of a rigid polymer of the matrix phase. In embodiments of the present invention, partial miscibility of rubbery phase can be controlled through adjustment of the MW of the rubbery polymer component and the relative MW of the rubbery and rigid polymer. Therefore, the rubber toughening can be controlled through the adjustment of the MW of the rubbery polymer component.

For a scaffold composition that is a blend of a rubbery polymer with a rigid polymer, the MW of the rubbery polymer component can be between 10% and 200% of the MW of the rigid polymer of the matrix phase. For a scaffold composition that is a blend of a rubbery block copolymer with a rigid polymer, the MW of the rubbery polymer block can be between 10% and 200% of the MW of the rigid polymer of the matrix phase. For a scaffold composition that is a rubbery block copolymer, the MW of the rubbery polymer block can be between 10% and 200% of the MW of the rigid polymer of the rigid polymer block. A rubbery polymer component with a higher MW that is 100-200% of that of the rigid polymer MW, such as PLLA, is expected to result in an immiscible, two phase blend. A rubbery polymer component with a MW less than 100% of the rigid polymer MW may provide partial miscibility or complete miscibility. The MW of the rubbery polymer component may be less than 25%, less than 50%, less than 75%, 25 to 50%, 50 to 75%, or 75 to 100% of the rigid polymer MW.

A low MW rubbery polymer component in the ranges less than the rigid polymer MW may provide partial miscibility of the rubbery polymer and the matrix phase. The increased miscibility of the two materials may provide greater plasticization of the blend.

For blends of rubbery polymers and copolymers with rigid polymers, the MW of the rigid polymer may be 50 to 100 kDa, 100 to 200 kDa, 100 to 300 kDa, 100 to 500 kDa, 100 to 600 kDa, 200 to 300 kDa, 300 to 400 kDa, 400 to 500 kDa, 400 to 600 kDa, 500 to 600 kDa, or greater than 600 kDa. The MW of a rubbery polymer blended with the rigid polymer may be 100 to 200% of the MW of the rigid polymer or less than 25%, 25 to 50%, 50 to 75%, or 75 to 100% of the rigid polymer. For example, the MW of the rubbery polymer can be less than 2 kDa, less than 20 kDa, 2 to 10 kDa, 10 to 50 kDa, 20 to 50 kDa, 20 to 100 kDa, 50 to 100 kDa, or greater than 100 kDa.

A rubbery block copolymer blended with a rigid polymer, such as PLLA-b-PCL, can have a MW less than 100% of the rigid polymer, for example, 30 to 500 kDa. The molar composition of the rubbery block(s) in the block copolymer may be between 20 and 80%, or more narrowly, 5 to 20%, 20 to 30%, 30 to 40%, or 40 to 50%, 50 to 60%, or 60 to 80%.

A random/alternating copolymer of a rubbery polymer blended with rigid polymer can have a MW less than 100% of the rigid polymer, or 30 to 500 kDa. The molar composition of the rubbery polymer in the copolymer may be between 20 and 80%, or more narrowly, 20 to 40%, 40 to 50%, 50 to 60%, or 60 to 80%. The remainder the copolymer may be completely the rigid polymer.

A block copolymer of a rigid polymer and rubbery polymer that forms all or almost all of the scaffold composition can have a MW of 50 to 100 kDa, 100 to 200 kDa, 200 to 300 kDa, 300 to 400 kDa, 400 to 500 kDa, 400 to 600 kDa, 500 to 600 kDa, or greater than 600 kDa. The composition of the rubbery blocks may be at least 0.2 wt or mol %, at least 0.5 wt %, 0.2 to 1 wt or mol %, 0.5 to 5 wt %, 1 to 5 wt or mol %, 5 to 15 wt or mol %, and 15-25 wt or mol %. This composition can be divided into one or more blocks in one of the various structure, linear block copolymer, star block copolymer, etc. For example, a linear block copolymer can be segmented into alternating rigid and rubbery blocks.

A random/alternating copolymer of a rigid polymer and rubbery polymer that forms all or almost all of the scaffold composition can have a MW of 50 to 100 kDa, 60 to 100 kDa, 100 to 200 kDa, 200 to 300 kDa, 300 to 400 kDa, 400 to 500 kDa, 500 to 600 kDa, or greater than 600 kDa. The composition of the rubbery blocks may be at least 0.2 wt, at least 0.5 wt %, mol %, 0.2 to 1 wt or mol %, 0.5 to 5 wt %, 1-5 wt or mol %, 5 to 15 wt or mol %, and 15-25 wt or mol %.

In a two-phase rubber toughened scaffold composition, it is believed that the rubber toughening varies with contact area or surface to volume ratio (S/V) between the matrix and dispersed phases. It is expected that fracture toughness increases as the S/V ratio between the phases increases. For a given w/w ratio of rubbery to rigid components, decreasing the size of the dispersed phase increases fracture toughness of the blend. Another way of increasing S/V of the rubbery to matrix phases is anisotropy or nonspherical shape of the rubbery domains for a given w/w ratio of rubbery to matrix phases. The ratio of the length to width of the domains may be 1.5:1 to 2:1, 2:1 to 3:1, 3:1 to 5:1, 5:1 to 10:1. Additionally, the domains may also be preferentially aligned along the cylindrical axis of the tube or scaffold or preferentially aligned circumferentially. In certain embodiments, a rubbery phase is an interconnected network structure throughout a tube or scaffold composition.

The anisotropic shape distribution may be induced in a polymeric tube prior to making the scaffold through various processing methods including extrusion, drawing, and/or biaxial expansion. Biaxial expansion refers to a process that includes both radial expansion and axial elongation of tube. The anisotropic shape processing step can be an additional step in the scaffold manufacturing process described herein or as part of this manufacturing process. The shape of the rubbery domains may be controlled by various processing conditions or parameters.

In some embodiments, a polymer tube is subjected to a drawing process after forming a tube by extrusion. The polymer tube can be drawn prior to the radial expansion of the tube. In the drawing step, the tube is axially elongated. The drawing can occur without any increase in tube diameter. Drawing the tube elongates the rubbery domains selectively in the axial direction.

The tube may be elongated by application of a tensile force at one or both ends of the tube. The tensile force may be constant or variable with time. Elongating the tube may be performed with machines obtained, for example, from Instron Corporation of Canton, Mass.

The polymer tube may further undergo biaxial expansion to enhance both radial and axial toughness and integrity in response to mechanical fatigue. In biaxial expansion, the polymer tube is radially expanded and axially elongated. A scaffold is then cut from the expanded/elongated tube. The tube may be radially expanded/elongated using a blow molding process described in 2011-0066222. The percent radial expansion (% RE) is defined as: $100\% \times (IDe/IDo-1)$, wherein IDe is the expanded inner diameter and IDo is the original diameter of the tube. The percent axial elongation (% AE) is defined as: $100\% \times (Le/Lo-1)$, Le is the elongated tube length and Le is the original tube length.

The % RE and % AE can be used to adjust the anisotropy and orientation of the rubbery domains through their magnitude and relative magnitude. The % RE may be 150 to 200%, 200 to 300%, 300 to 400%, or greater than 400%. The % AE may be 110 to 120%, 120 to 130%, or 130 to 150%, or greater than 150%. Any combination of these ranges of % RE and % AE may be used.

The processing temperature of the drawing and biaxial expansion can be done at various temperatures above or below the Tg of the rigid polymer, for example, at a temperature range of 50% to 250% of the Tg of the rigid polymer ($T_{g,\ rigid}$). For example, for PLLA, the temperature range can be between ambient temperature (20-30 deg C.) to 150 deg C. The processing temperature of the drawing may be between the Tg and Tm of the rubbery component or above the Tm of the rubbery component. The processing temperature will influence the shape of the rubbery phase, its relative orientation, and the crystallinity of the matrix phase. The processing temperature may refer to the measured temperature of a polymer tube during the processing or a medium used to heat the polymer tube during processing, e.g., warm gas.

In the drawing process, the polymer tube may be held under tension for a selected time at the processing temperature. The rubbery phase may be preferentially elongated during drawing (versus the matrix phase) by using a temperature, $T_{elong\#1}$, $$T_{g,\ rubber} < T_{elong\#1} < T_{g,\ rigid}$$

where $T_{g,\ rubber}$ is the Tg of the rubbery component and $T_{g,\ rigid}$ of the rigid polymer in the matrix phase. More narrowly the processing temperature range can include any subrange, for example, 5 deg C. subranges between $T_{g,\ rubber}$ and $T_{g,\ rigid}$.

A higher degree of elongation of the rubbery phase and also some axial orientation of the matrix phase may be obtained with a temperature of elongation, $T_{elong\#2}$, $$T_{m,\ rubber},\ T_{g,\ rigid} < T_{elong\#2} < T_{m,\ rigid}$$

where, $T_{m,\ rubber}$ is the melting temperature of the rubbery polymer component and $T_{m,\ rigid}$ is the melting temperature of the rigid polymer. More narrowly the processing temperature range can include any subrange, for example, in 5 deg C. subranges between $T_{m,\ rubber}$, $T_{g,\ rigid}$ and $T_{m,\ rigid}$. During extrusion maximal elongation of both phases will occur at a temperature greater than the melting temperature of either phase.

After drawing or biaxial orientation, the cooling rate from the processing temperature may influence the retention of induced orientation. In some embodiments, the polymer tube can be cooled immediately below $T_{m, rubber}$ and $T_{g\ rigid}$. The immediate cooling can be performed by quenching the tube in a cold water bath. Alternatively, the polymer tube can be cooled at a controlled rate from the processing temperature. The controlled cooling provides additional time for the rigid polymer to crystallize and provides time for mixing of the rubbery phase. An exemplary cooling rate is range is 10 to 30 deg C./min. Maintaining the tube or scaffold at a temperature below Tg, rubber, will enable further retention of the amorphous orientation during storage, but calls for an ultra low storage temperature, as shown in Table 1.

In further embodiments, the scaffold composition can include a rubbery polymer component that is crosslinked. Additionally, the rubbery polymer may be crosslinked with the rigid polymer at the interface of a rubbery phase and the matrix phase, thus increasing interfacial bonding. The crosslinking of the rubbery phase is expected to increase the elastic response of the rubbery phase and reduce or eliminate hysteresis of the scaffold composition upon loading and unloading. [can meaning of "elastic response" be clarified or specified]

As used herein, crosslinks refer generally to chemical covalent bonds that link one polymer chain to another. A crosslinked polymer includes crosslinks throughout a polymer material sample. When polymer chains are linked together by crosslinks, they lose some of their ability to move as individual polymer chains, thus stabilizing the polymer.

Crosslinks can be formed by chemical reactions that are initiated by heat, pressure, crosslinking agents, and/or radiation. The radiation can include, but is not limited to, electron beam, gamma, or UV light. The crosslinking induced by radiation can be caused by or facilitated by a crosslinking agent. A crosslinking agent is a substance or compound that promotes or regulates intermolecular covalent bonding between polymer chains, linking them together to create a more rigid structure. The crosslinking agent is a compound that is separate and distinct from the polymer chains prior to the crosslinking between which it promotes or regulates bonding.

In some embodiments, the scaffold composition includes a rubbery polymer component, a rigid polymer component, or both that is crosslinkable due to formation of links or bonds between different moieties or functional groups of the polymers when exposed to radiation. Such polymers are referred to as self-crosslinkable polymers since crosslinks form in the absence of a crosslinking agent. The crosslinking can be due entirely to crosslinking between the moieties or functional groups of the polymer. In other embodiments, the polymer can additionally include a crosslinking agent so that crosslinking is due to the crosslinking agent and a self-crosslinking mechanism.

In some embodiments, the self-crosslinkable polymer can be a copolymer that includes reactive functional groups and functional groups that form biodegradable rubbery or rigid polymers when polymerized or copolymerized. The latter functional groups (referred to as degradable functional groups) are derived from monomers that include, but are not limited to L-lactic acid, glycolic acid, ε-caprolactone, dioxanone, D-lactic acid, trimethylene carbonate, 4-hydroxy butyrate, and butylene succinate. The reactive functional groups can include alkenes (e.g., acrylates) or alkynes. "Reactive" refers to upon exposure of the polymer to radiation, crosslinking is induced at the reactive functional groups. Radiation can include, for example, electron beam or gamma radiation. The self-crosslinkable polymer can be formed through copolymerization of compounds that have the reactive functional groups and a monomer, such as lactic acid, to form a biodegradable, crosslinkable polymer. The self-crosslinkable copolymer can be a random or alternating copolymer. Further details on forming self-crosslinkable biodegradable polymer components can be found in US2010/0262223.

In some embodiments, a tube or scaffold includes a rubbery polymer component that is self-crosslinkable. The rubbery polymer is crosslinked by exposing the tube or scaffold to radiation. The radiation induces crosslinking in the rubbery polymer. The radiation may also induce crosslinking between the rubbery polymer with the rigid polymer.

The tube may be exposed to radiation to induce crosslinking after extrusion and before drawing or biaxial expansion process steps. Alternatively, the tube may be exposed to radiation after drawing or biaxial expansion steps. A scaffold may be exposed to radiation to induce crosslinking in an as-cut expanded state. Alternatively, a scaffold may be exposed to radiation to induce crosslinking in a crimped state.

Additionally or alternatively, crosslinking of the tube or scaffold can be accomplished using crosslinking agents. A radiation sensitive crosslinking compound can be blended with a scaffold composition during processing such as extrusion or during a solution based treatment. The crosslinking agent can be mixed or dispersed within the bioresorbable polymer of the tube. When the tube is exposed to radiation, the crosslinking agent induces crosslinking of the bioresorbable polymer.

Exemplary crosslinking agents include triallyl isocyanurate (TAIC), trimethally isocyanurate (TMAIC), tripropylene glycol diacrylate (TPGDA) and trimethylolpropane triacrylate (TMPTA), however, other crosslinking agents may be used such as bis-ε-caprolactone and similar structures.

In some embodiments, the crosslinking agent can be mixed with rubbery and rigid components in an extruder. In embodiments that the composition is a polymer blend, the crosslinking agent can be melt blended with the rubbery polymer or a copolymer with a rubbery polymer component first. This blend may then be blended with rigid polymer. The separate blending may preferentially distribute the crosslinking agent in the rubbery polymer or copolymer and limit the degree of crosslinking in the matrix phase.

The degree of crosslinking depends on the weight percent of the crosslinking agent and the radiation dose. The tube may include an amount of crosslinking agent sufficient to provide a desired crosslink density or gel fraction. In exemplary embodiments, the tube includes less than 1 wt %, 1-3 wt %, 3-5 wt %, or greater than 5 wt % crosslinking agent. The remaining material of the tube can be the bioabsorbable polymer or consist essentially of the bioabsorbable polymer.

The radiation crosslinking can be performed at various temperatures of the tube or scaffold. The temperature may be at least $T_{g,\ rubber}$, in particular, between $T_{g,\ rubber}$ and $T_{g,\ rigid}$. More narrowly, the temperature may be at or near ambient temperature, for example, 20 to 30 deg C. The temperature may also be greater than $T_{g,\ rigid}$ and less than $T_{m,\ rigid}$. The temperature may also be greater than $T_{m,\ rubber}$ such that the rubbery polymer is in a molten state. The crosslinking may be enhanced by using a lower MW rubbery component relative to PLLA (less than 25%, 25 to 50%, 50 to 75% of the MW of the rigid polymer) to increase the concentration of functional end-groups.

The radiation dose for crosslinking of a self-crosslinkable composition or one containing crosslinking agent can be 0.1-100 kGy, 10-100 kGy, 0.1-10 kGy, 10-20 kGy, 20 to 30 kGy, 20 to 31, kGy, 30-40 kGy, or more narrowly 25-30 kGy.

Radiation also induces chain scission in polymers. It may be desirable for the rate of crosslinking to be greater than the rate of chain scission. The rate of chain scission is favored at higher doses. Therefore, a lower radiation dose that preferentially induces crosslinking over chain scission may be preferred, for example, 0 to 10 kGy or 10 to 20 kGy.

Additionally, antioxidants or free radical scavengers may be added to reduce any irradiation induced oxidation. "Free radical scavengers" or "antioxidants" are molecules that slow or prevent the oxidation of other chemicals. Free radical scavengers or antioxidants can remove free radical intermediates that can participate in chain reactions, thus terminating such reactions. Free radical scavengers or antioxidants can also inhibit other oxidation reactions by being oxidized themselves. The free radical scavengers or antioxidants can be melt blended with the polymer composition during extrusion.

Various free radical scavengers and antioxidants, both synthetic or natural, may be used to reduce or prevent chemical degradation in the scaffold composition. Representative examples of free radical scavengers or antioxidants that can reduce or eliminate chemical degradation due to radiation include, L-ascorbate (Vitamin C), Vitamin E, herbal rosemary, sage extracts, glutathione, melatonin, carotenes, resveratrol, butylated hydroxyanisole, butylated hydroxytoluene, propyl gallate, tertbutylhydroquinone, and combinations thereof. Various isomers of Vitamin E may be used, including the four tocopherols, and four tocotrienols. The alpha, beta, gamma and delta forms of both the tocopherols and tocotrienols may be used to prevent chemical degradation. In particular, butylated hydroxytoluene can be used in drug-polymer layers to reduce or prevent degradation of active agents.

Low molecular weight free radical scavengers or antioxidants may be susceptible to leaching from polymer materials. Thus, such free radical scavengers or antioxidants may at least partially leach out of the scaffold composition. Oligomeric or polymeric free radical scavengers or antioxidants are less susceptible to leaching from polymers. Thus, some embodiments can include using oligomeric or polymeric free radical scavengers or antioxidants in the scaffold composition. Representative examples of oligomeric or polymeric free radical scavengers or antioxidants include, but are not limited to, oligomeric or polymeric proanthocyanidins, polyphenols, polyphosphates, polyazomethine, high sulfate agar oligomers, chitooligosaccharides obtained by partial chitosan hydrolysis, polyfunctional oligomeric thioethers with sterically hindered phenols. Some polymeric free radical scavengers can be bonded or grafted on the backbone of a polymer to be protected and blended with additional polymer.

It may be advantageous to minimize or control the crystallinity of the rigid polymer (e.g., PLLA) prior to radiation crosslinking Highly crystalline PLLA preferentially experiences MW decrease from radiation as compared to amorphous PLLA. Radiation crosslinking a tube with lower crystallinity may result in more efficient crosslinking compared to a higher crystallinity tube. The crystallinity of the tube prior to crosslinking may be less than 15%, 15 to 30%, or 30 to 40%, or less than 40%.

In further embodiments, the scaffold composition can include a blend of PLLA and poly(d-lactide) or a blend of PLLA and poly(DL-lactide). Alternatively the polymer can have various ratios of D-lactide and L-lactide. Some of these polymers may form stereocomplexes. The stereocomplex can be made more rigid and tough via radiation crosslinking in the solid state. In another example a softer, PLLA-PCL 90-10 copolymer may become more rigid via crosslinking in the solid state by gamma irradiation with or without the presence of a crosslinking agent and antioxidant.

It is believed that SFA scaffolds, such as those disclosed above, made from some or all of the compositions disclosed herein may be deployed from a crimped diameter (e.g., 1.8 to 2.2 mm or 2 mm) to a diameter of 4.5 to 8 mm with no broken struts and no cracks. Additionally, such scaffolds may have a radial strength, as measured by techniques described herein and in cited applications, of greater than about 0.3 N/mm, or between about 0.3 and 1.2 N/mm or between about 0.3 and 1.2 N/mm, and a radial stiffness of greater than about 0. N/mm or between about 0.3 N/mm and 2 N/mm.

The fabrication methods of a bioabsorbable stents described herein can include the following steps:
(1) forming a polymeric tube using extrusion,
(2) radially deforming the formed tube,
(3) forming a stent scaffolding from the deformed tube by laser machining a stent pattern in the deformed tube with laser cutting,
(4) optionally forming a therapeutic coating over the scaffolding,
(5) crimping the stent over a delivery balloon, and
(6) sterilization with election-beam (E-Beam) radiation.

In the extrusion step, a polymer is processed in an extruder above the melting temperature of the rubbery and rigid polymer components. The component of a blend of the composition described above can be combined and mixed in the extruder. Where applicable, additives such as crosslinking agents or antioxidants can be added to the polymer and mixed in the extruder. Alternatively, the additives may be mixed in a separate step with some of the polymer to form a mixture having higher concentration(s) than the final concentration(s) of the product. The high concentration polymer mixture can then be added to additional polymer in the extruder to form a polymer tube.

In step (2) above, the extruded tube may be radially deformed to increase the radial strength of the tube, and thus, the finished stent. The increase in strength reduces the thickness of the struts required to support a lumen with the scaffold when expanded at an implant site. In exemplary embodiments, the strut thickness can be 100-200 microns, or more narrowly, 120-180, 130-170, or 140-160 microns.

Detailed discussion of the manufacturing process of a bioabsorbable stent can be found elsewhere, e.g., U.S. Patent Publication No. 20070283552, which is incorporated by reference herein.

"Molecular weight" refers to either number average molecular weight (Mn) or weight average molecular weight (Mw).

"Semi-crystalline polymer" refers to a polymer that has or can have regions of crystalline molecular structure and amorphous regions. The crystalline regions may be referred to as crystallites or spherulites which can be dispersed or embedded within amorphous regions.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. The modulus typically is the initial slope of a stress—strain curve at low strain in the linear region. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

EXAMPLE 1

PLLA (Purac) is blended with P4HB (Tepha) at either 95:5, 90:10, 85:15 or 80:20 by weight at 180° C. higher temperature in a co-rotating compounding extruder into tubing of 0.051" ID and 0.139" OD. To implement biaxial orientation and mechanical stiffness, tubing is later expanded to 7 mm OD and 0.11" wall thickness at 110 deg C. or lower temperature with the horizontal hot air expander. The expanded tubing is then laser cut to the V62 SFA BVS scaffold pattern. The scaffold is then spray coated with everolimus:PDLLA 1:1 at a 100 ug/cm$^2$ dose. The drug coated scaffold is then crimped to 0.092"OD or less with a MSI crimper at 48° C., sheathed, packaged under Ar and sterilized with electron beam. The resulting scaffold will have increased fracture toughness when tested in in vitro and preclinical fatigue models.

EXAMPLE 2

Measurements of properties were performed of bioresorbable scaffolds made of 100% PLLA and bioresorbable scaffolds made of 95 wt % PLLA and 5% PEG. The molecular weight of the PEG was at least 2 kDa. The scaffold patterns were the V23 pattern as described in US2011/0190872 and US2011/0190871. The three scaffolds tested were:
  (1) 100% PLLA; wall thickness=0.008 in
  (2) 100% PLLA; wall thickness=0.014 in
  (3) 100% PLLA/PEG; wall thickness=0.008 in
The scaffolds tested had a coating composed of 50 wt % PDLLA and 50 wt % Zotarolimus (ABT-578). The as-cut or initial diameter before crimping is 7 mm and the width of the struts is approximately 0.011 in.

The following properties were tested: radial strength, radial stiffness, acute recoil, deploy to fracture, acute fracture, and crush recovery.

Figure 2:
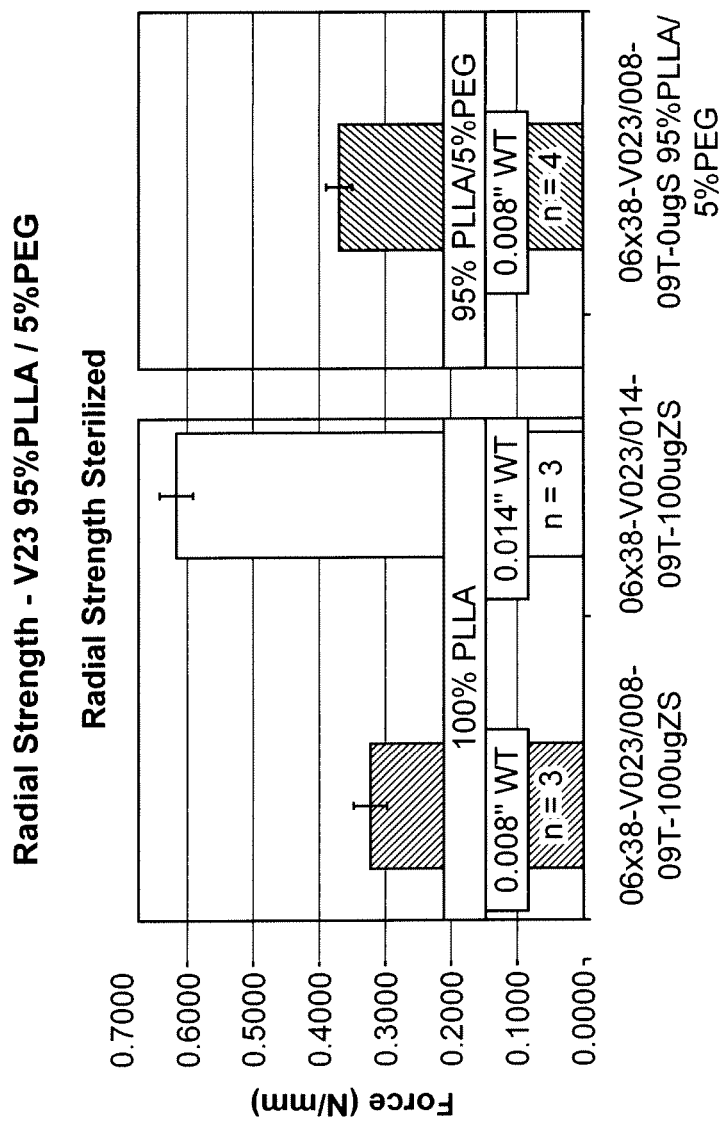
FIG. 2 depicts the measured radial strength of the PLLA scaffolds.

FIG. 2 depicts the measured radial strength of the PLLA scaffolds with 0.008 in and 0.014 wall thickness and PLLA/PEG scaffold with 0.008 in wall thickness. The PLLA/PEG scaffold has a higher radial strength than the PLLA scaffold with the 0.008 in wall thickness.

Figure 3:
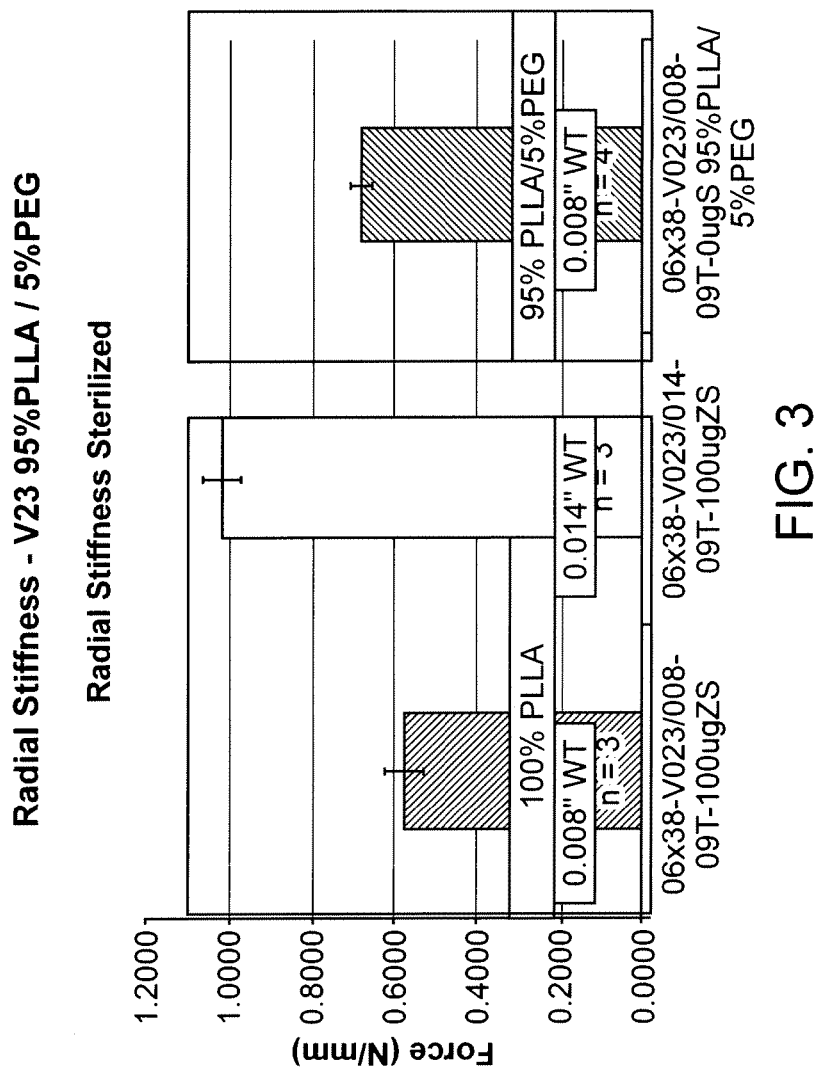
FIG. 3 depicts the measured radial stiffness of the PLLA scaffolds.

FIG. 3 depicts the measured radial stiffness of the PLLA scaffolds with 0.008 in and 0.014 wall thickness and PLLA/PEG scaffold with 0.008 in wall thickness. The PLLA/PEG scaffold has a higher radial stiffness than the PLLA scaffold with the 0.008 in wall thickness.

The acute recoil is tested by crimping the scaffolds to over a delivery balloon. The scaffolds are then expanded. The balloon is deflated and the amount of recoil from the expanded diameter is measured. The percentage recoil is shown in Table 2.

Table 2 provides acute recoil for the three scaffolds.

| Scaffold | Percentage Recoil |
|---|---|
| #1 | 3.3 ± 0.6% |
| #2 | 3.6 ± 0.6% |
| #3 | 2.4 ± 0.6% |

For the test of scaffold #3, the scaffold remained attached to the deployment block after balloon deflation. In the tests for scaffolds #1 and #2, the scaffold slid out from the deployment block after balloon deflation.

Figure 4:
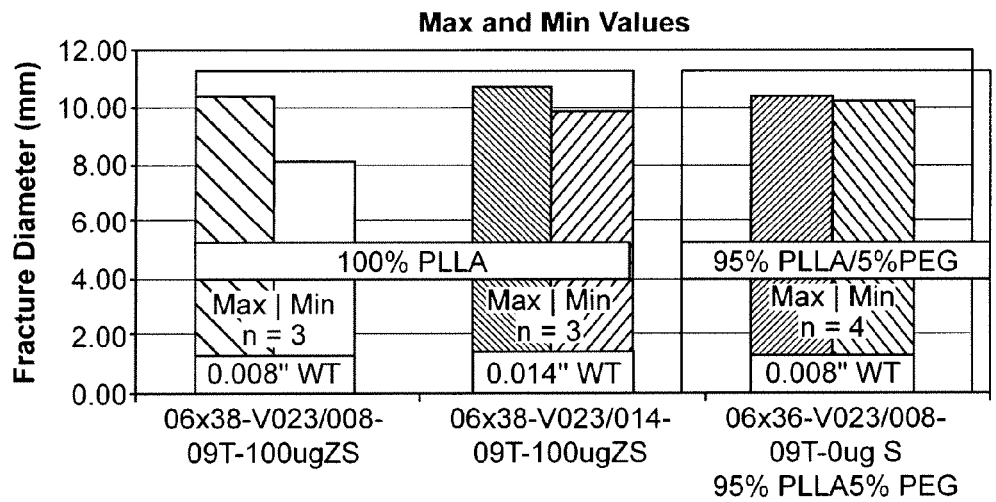
FIG. 4 depicts the minimum and maximum diameter of deploy to fracture was observed.
Figure 5:
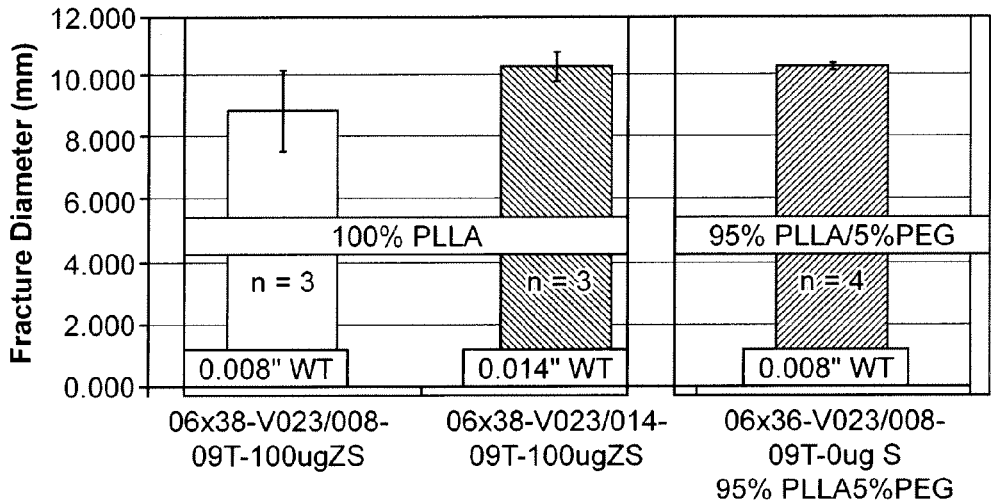
FIG. 5 depicts the minimum and maximum diameter of deploy to fracture was observed.

In the tests of the deploy to fracture, the scaffolds were expanded by a delivery balloon until the first appearance of fractures in the scaffold. FIG. 4 depicts the minimum and maximum diameter of deploy to fracture was observed. The minimum deploy to fracture observed is about the same for scaffold #1 and #3. The minimum deploy to fracture for scaffold #3 is significantly higher than for scaffold #1. FIG. 5 depicts the average deploy to fracture of the scaffolds, which shows that the average deploy to fracture is higher than for scaffold #1.

Table 3 depicts the number and size of cracks observed in the acute fracture tests. The PLLA/PEG scaffold (#3) has significantly fewer cracks.

TABLE 3

Distribution of cracks in acute fracture tests.

| Scaffold | Minor Cracks | Moderate Cracks | Severe Cracks | Fractures | Total Cracks |
|---|---|---|---|---|---|
| #3 | 27 ± 4 | 3 ± 1.5 | | | 32 ± 4 |
| #1 | 47 ± 13 | 30 ± 13 | 27 ± 4 | 7 ± 7 | 84 ± 33 |

Figure 6:
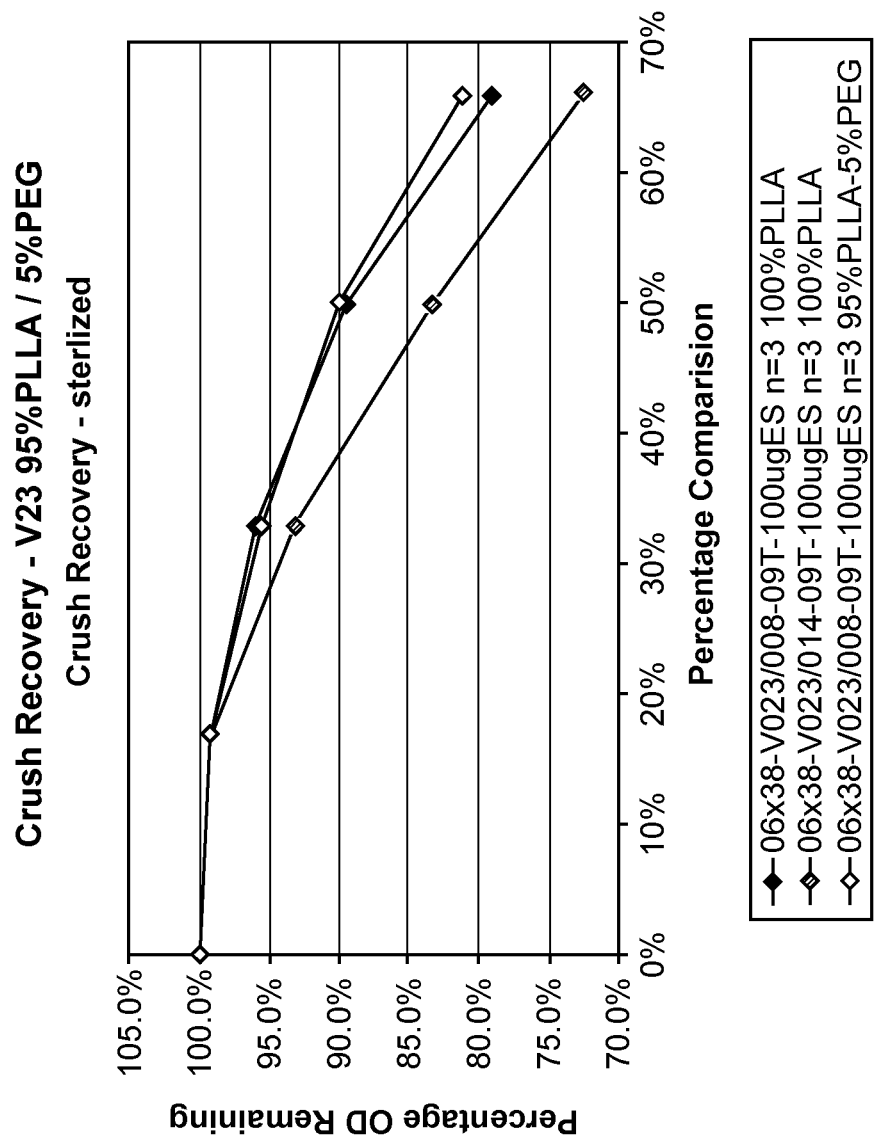
FIG. 6 depicts the results of crush recovery tests for two scaffolds.

FIG. 6 depicts the results of crush recovery tests for two scaffolds, #1 to #3.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical device, comprising:
a scaffold formed from a polymer tube,
configured for being plastically deformed when crimped to a balloon having a nominal inflation diameter,
the scaffold comprising a plurality of rings, each of the rings having ring struts interconnected at hinge portions, such that the ring struts and hinge portions form a unitary ring,
the scaffold having an expanded diameter when plastically deformed from a crimped state by the balloon inflated to the nominal inflation diameter, and
the hinge portions are plastically deformed when the scaffold is crimped to the balloon and when the scaffold is expanded by the balloon;
wherein the scaffold attains greater than 80% of its expanded diameter after being crushed to at least 50% of its expanded diameter; and
wherein the scaffold is made from a composition including a rigid bioresorbable polymer component having a glass transition temperature (Tg) greater than 37 deg C. and a rubbery polymer component having a Tg less than ambient temperature, wherein the rubbery polymer component is between 1 to 10 wt % of the composition.

2. A medical device, comprising:
a scaffold formed from a polymer tube,
configured for being plastically deformed when crimped to a balloon having a nominal inflation diameter,
the scaffold comprising a plurality of rings, each of the rings having ring struts interconnected at hinge portions, such that the ring struts and the hinge portions form a unitary ring,
the scaffold having an expanded diameter when plastically deformed from a crimped state by the balloon inflated to the nominal inflation diameter, and
the hinge portions are plastically deformed when the scaffold is crimped to the balloon and when the scaffold is expanded by the balloon;
wherein the scaffold attains greater than 80% of its expanded diameter after being crushed to at least 50% of its expanded diameter;
wherein the scaffold is made from a composition including a rigid bioresorbable polymer component having a glass transition temperature (Tg) greater than 37 deg C. and a rubbery polymer component having a Tg less than ambient temperature, wherein the rubbery polymer component is between 5 and 25 wt % of the composition; and
wherein the scaffold has a wall thickness of between 0.2 and 0.4 mm and a pre-crimp diameter of between 5-10 mm.

3. The stent of claim 2, wherein the rubbery polymer component is polyethylene glycol (PEG) having a weight average molecular weight (Mw) of 20 kDa or less.

4. The stent of claim 2, wherein the rubbery polymer component is PEG and the PEG is 5 to 10 wt % of the scaffold.

5. The stent of claim 2, wherein the rigid bioresorbable polymer is about 75 to 95 wt % of the scaffold and the rubbery polymer is 5 to 25 wt % of the scaffold.

6. The stent of claim 2, wherein the scaffold has a deploy-to-fracture diameter of about 10 mm and a wall thickness of 0.2 mm.

7. The stent of claim 2, wherein the scaffold has a deploy-to-fracture diameter of between 8 mm and 10 mm and a wall thickness of 0.2 mm.

8. The stent of claim 2, wherein the scaffold has a pre-crimp diameter of 6-8 mm, a deploy-to-fracture diameter of between about 8 mm and 10 mm and a wall thickness of 0.2 mm.

9. The medical device of claim 1, wherein the rubbery polymer component is polycaprolactone (PCL).

\* \* \* \* \*